(12) United States Patent
Matsuoka (10) Patent No.: US 12,155,937 B2
(45) Date of Patent: Nov. 26, 2024

(54) IMAGING CONTROL DEVICE, ENDOSCOPE SYSTEM, AND IMAGING CONTROL METHOD

(71) Applicant: JVCKENWOOD Corporation, Yokohama (JP)

(72) Inventor: Kenji Matsuoka, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 124 days.

(21) Appl. No.: 18/180,162

(22) Filed: Mar. 8, 2023

(65) Prior Publication Data

US 2023/0224593 A1    Jul. 13, 2023

Related U.S. Application Data

(63) Continuation of application No. PCT/JP2021/023109, filed on Jun. 17, 2021.

(30) Foreign Application Priority Data

Sep. 17, 2020   (JP) .................................. 2020-156797

(51) Int. Cl.
*A61B 1/045*       (2006.01)
*A61B 1/06*        (2006.01)
(Continued)

(52) U.S. Cl.
CPC .............. *H04N 23/71* (2023.01); *A61B 1/045* (2013.01); *A61B 1/06* (2013.01); *G06T 7/11* (2017.01);
(Continued)

(58) Field of Classification Search
CPC ...... H04N 23/71; H04N 23/555; H04N 23/56; A61B 1/045; A61B 1/06; A61B 1/000095;
(Continued)

(56) References Cited

U.S. PATENT DOCUMENTS

| 2014/0081083 | A1* | 3/2014 | Morita | ............... | A61B 1/00177 600/109 |
| 2016/0128545 | A1* | 5/2016 | Morita | ................. | A61B 1/0005 600/109 |

(Continued)

FOREIGN PATENT DOCUMENTS

JP    2011-139760    7/2011

OTHER PUBLICATIONS

International Search Report and Written Opinion for International Application No. PCT/JP2021/023109 mailed on Sep. 7, 2021, 8 pages.

*Primary Examiner* — John W Miller
*Assistant Examiner* — Humam M Satti
(74) *Attorney, Agent, or Firm* — Amin, Turocy & Watson, LLP (57) ABSTRACT

An imaging control device includes: a region dividing unit that divides a taken image into a plurality of regions; a luminance value calculating unit that calculates the average luminance value of each region obtained by division by the region dividing unit; a region identifying unit that identifies a region in which the average luminance value calculated by the luminance value calculating unit is equal to or greater than a predetermined threshold value; a photometric range deciding unit; and a signal processing unit.

5 Claims, 6 Drawing Sheets (51) Int. Cl.
  *G06T 7/11*    (2017.01)
  *H04N 23/50*   (2023.01)
  *H04N 23/56*   (2023.01)
  *H04N 23/71*   (2023.01)

(52) U.S. Cl.
  CPC ........... *H04N 23/555* (2023.01); *H04N 23/56* (2023.01); *G06T 2207/10068* (2013.01); *G06T 2207/20021* (2013.01); *G06T 2207/30004* (2013.01)

(58) Field of Classification Search
  CPC ... A61B 1/00188; A61B 1/00009; G06T 7/11; G06T 2207/10068; G06T 2207/20021; G06T 2207/30004
  See application file for complete search history.

(56) References Cited

U.S. PATENT DOCUMENTS

2019/0158760 A1* 5/2019 Shibata ................ H04N 23/673
2019/0313002 A1* 10/2019 Wu ....................... H04N 23/71

* cited by examiner

IMAGING CONTROL DEVICE, ENDOSCOPE SYSTEM, AND IMAGING CONTROL METHOD

CROSS-REFERENCE TO RELATED APPLICATION(S)

This application is a Continuation of PCT international application Ser. No. PCT/JP2021/023109 filed on Jun. 17, 2021 which designates the United States, incorporated herein by reference, and which claims the benefit of priority from Japanese Patent Application No. 2020-156797, filed on Sep. 17, 2020, incorporated herein by reference.

BACKGROUND

1. Technical Field

The present disclosure relates to an imaging control device, an endoscope system, and an imaging control method.

2. Description of the Related Art

A technology is known in which, during a laparoscopic surgery performed using a rigid endoscope, autofocusing of an imaging device is controlled by excluding the body parts that are not appropriate as the focus position of the imaging device (for example, refer to Japanese Patent Application Laid-open No. 2011-139760).

In Japanese Patent Application Laid-open No. 2011-139760, autofocus control is prevented from being performed at a body part that is not appropriate for focusing. Hence, an inappropriate body part is prevented from coming into focus. However, when the focus is on any one of a plurality of unexcluded body parts, there is a possibility that the body part in focus is not the operator-desired body part. This issue is not limited to autofocusing control, but is identical across the overall imaging auto-control such as automatic gain control and automatic white balance control.

SUMMARY

An imaging control device according to an embodiment of the present disclosure comprising: a region dividing unit that divides a taken image into a plurality of regions; a luminance value calculating unit that calculates average luminance value of each region obtained by division by the region dividing unit; a region identifying unit that identifies a region in which the average luminance value calculated by the luminance value calculating unit is equal to or greater than a predetermined threshold value; a photometric range deciding unit that, when period of time for which average luminance value of the region identified by the region identifying unit is equal to or greater than the threshold value is a period of time equal to or greater than a first predetermined period and smaller than a second predetermined period, decides that the region identified by the region identifying unit represents a new photometric range; and a signal processing unit that performs imaging auto-control with respect to the new photometric range decided by the photometric range deciding unit.

An endoscope system according to an embodiment of the present disclosure comprising: the imaging control device according to an embodiment of the present disclosure; an imaging device that, under control of the imaging control device, takes image of an affected area; and a light source that is installed in the imaging device and that bombards light onto the affected area, wherein the imaging control device decides on new photometric range based on change in luminance value attributed to reflected light that is formed by reflection of the light, which is bombarded by the light source unit, from a procedure tool.

An imaging control method according to an embodiment of the present disclosure comprising: a step for dividing a taken image into a plurality of regions; a step for calculating average luminance value of each region obtained by division; a step for identifying a region in which the calculated average luminance value is equal to or greater than a predetermined threshold value; a step for deciding that, when period of time for which average luminance value of the identified region is equal to or greater than the threshold value is a period of time equal to or greater than a first predetermined period and smaller than a second predetermined period, includes deciding on the identified region as a new photometric range; and a step for performing imaging auto-control with respect to the new photometric range.

DETAILED DESCRIPTION OF THE PREFERRED EMBODIMENTS

An exemplary embodiment of the application concerned is described below in detail with reference to the accompanying drawings. However, the application concerned is not limited by the embodiment. Moreover, when a plurality of embodiments is present, it is possible to have combinations of the embodiments. In the embodiment described below, identical constituent elements are referred to by the same reference numerals, and their explanation is not repeatedly given.

Embodiment

Figure 1:
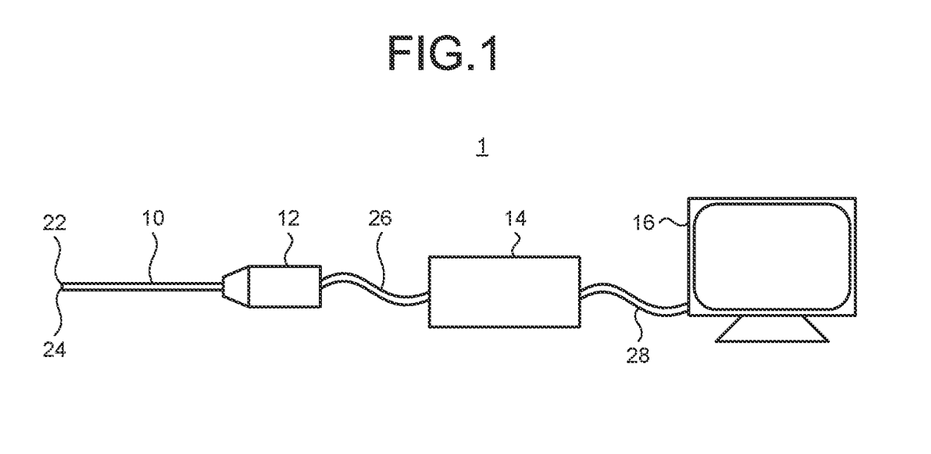
FIG. 1 is a diagram that schematically illustrates an exemplary configuration of an endoscope system according to an embodiment.

Explained below with reference to FIG. 1 is an endoscope system according to the embodiment. FIG. 1 is a diagram that schematically illustrates an exemplary configuration of the endoscope system according to the embodiment.

As illustrated in FIG. 1, an endoscope system 1 includes a rigid mirror 10, a camera head 12, a CCU (Camera Control Unit) 14, and a display device 16. The endoscope system 1 obtains in-vivo images using the rigid mirror 10 and the camera head 12. For example, the endoscope system 1 is used by an operator such as a doctor during a laparoscope surgery.

The rigid mirror 10 has an elongated tubular shape and is rigid in nature. The rigid mirror 10 is inserted into the body of a patient. For example, the rigid mirror 10 is inserted into the abdominal region of a patient. The rigid mirror 10 is configured using a plurality of optical lenses 22. At the front end thereof, the rigid mirror 10 includes a light source unit 24 that bombards a light supplied from a light source device (not illustrated). Thus, the light source unit 24 bombards a light into the body of the patient. The light bombarded by the light source unit 24 is collected by the optical lenses 22. As a result, an optical image is generated. The optical image that is generated as a result of light collection by the optical lenses 22 is then output to the camera head 12. Meanwhile, in the present embodiment, although the endoscope system 1 includes the rigid mirror 10, it can alternatively include a flexible mirror as the endoscope.

The camera head 12 performs imaging with respect to the optical image obtained from the rigid mirror 10, and outputs the imaging result. The camera head 12 performs imaging with respect to the optical image, which is formed as a result of light collection in the rigid mirror 10, under the control of the CCU 14; and outputs an imaging signal. The camera head 12 and the CCU 14 are connected by a cable 26. Thus, the camera head 12 outputs the imaging signal to the CCU 14 via the cable 26. The camera head 12 can also be called an imaging device. Regarding a configuration of the camera head 12, the explanation is given later.

The CCU 14 comprehensively controls the camera head 12 and the display device 16. The CCU 14 processes the imaging signal that is input from the camera head 12 via the cable 26, and generates an image signal. Then, the CCU 14 outputs the image signal to the display device 16. As a result, an image gets displayed in the display device 16. The CCU 14 and the display device 16 are connected by a cable 28. Thus, the CCU 14 outputs the image signal to the display device 16 via the cable 28. The CCU 14 can also be called an imaging control device. Regarding a configuration of the CCU 14, the explanation is given later.

The display device 16 displays images. For example, based on an image signal input from the CCU 14, the display device 16 displays a biological image of the patient. The display device 16 is a display such as a liquid crystal display (LCD) or an organic EL (Organic Electro-Luminescence) display.

In the present embodiment, imaging auto-control is performed based on the changes occurring in the luminance value of a taken image that is taken during a medical procedure. For example, when there is a movement of a procedure tool (for example, a surgical knife), there a change in the concerned portion. Particularly, a metallic procedure tool reflects the illumination light coming from the light source unit 24, thereby resulting in an increase in the luminance value. In that regard, the operator can use the illumination light and the procedure tool to temporarily and intentionally reflect the light so as to create a location within a specific region inside the body at which the luminance value becomes equal to or greater than a predetermined threshold value, and hence can specify the location on which attention is to be focused during the procedure. In the present embodiment, the location having the luminance value to be equal to or greater than the threshold value is determined to be the region on which the operator wishes to focus attention, and optimum imaging auto-control is performed with respect to that region.

[Configuration of Imaging Device]

Figure 2:
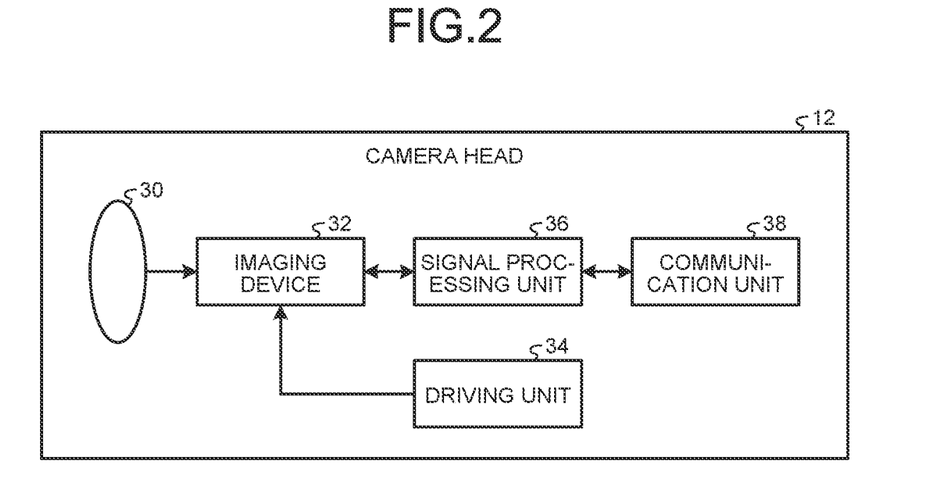
FIG. 2 is a block diagram illustrating an exemplary configuration of an imaging device according to the embodiment.

Explained below with reference to FIG. 2 is an exemplary configuration of the imaging device according to the embodiment. FIG. 2 is a block diagram illustrating an exemplary configuration of the imaging device according to the embodiment.

The camera head 12 includes an optical lens 30, an imaging device 32, a driving unit 34, a signal processing unit 36, and a communication unit 38.

The optical lens 30 can be configured using one or more lenses. The optical lens 22 can also serve as the last-stage lens of the rigid mirror 10. The optical lens 30 is configured to be movable along the light axis. As a result of being movable along the light axis, the optical lens 30 is equipped with a zooming function for varying the angle of view and a focusing function for varying the focal position. An optical image passes through the optical lens 30 and gets input to the imaging device 32.

The imaging device 32 takes images of a photographic subject under the control of the driving unit 34. The imaging device 32 receives the optical image formed by the optical lens 22, and converts the optical image into an electrical signal. For example, the imaging device 32 performs photoelectric conversion of the received optical image to convert it into an electrical signal (analog signal), and outputs the electrical signal to the signal processing unit 36. The imaging device 32 can be implemented using, for example, a CCD (Charge Coupled Device) image sensor or a CMOS (Complementary Metal Oxide Semiconductor).

The driving unit 34 controls the entire camera head 12 according to an operation signal corresponding to an operation input by the user via an operating unit (not illustrated), and according to a driving signal received from the CCU 14. For example, the driving unit 34 controls the zooming function and the focusing function of the optical lens 30, and varies the magnification and the focal point of the taken image obtained by the imaging device 32.

The signal processing unit 36 performs a variety of signal processing with respect to the signal received from the imaging device 32. For example, the signal processing unit 36 performs A/D (Analog/Digital) conversion with respect to the signal received from the imaging device 32, and generates an imaging signal. Then, the signal processing unit 36 outputs the generated imaging signal to the communication unit 38.

The driving unit 34 and the signal processing unit 36 are implemented when, for example, a CPU (Central Processing Unit) or an MPU (Micro Processing Unit) execute a program, which is stored in a memory unit (not illustrated), using a RAM as the work area. Alternatively, the driving unit 34 and the signal processing unit 36 can be implemented using an integrated circuit such as an ASIC (Application Specific Integrated Circuit) or an FPGA (Field Programmable Gate Array). Still alternatively, the driving unit 34 and the signal processing unit 36 can be implemented using a combination of software and hardware.

The communication unit 38 sends a variety of information to and receives a variety of information from the CCU 14. For example, the communication unit 38 converts the imaging signal, which is received from the signal processing unit 36, into a predetermined signal format to be output to the CCU 14. Then, the signal processing unit 36 outputs the imaging signal, which has been converted into a predetermined signal format, to the CCU 14. Moreover, the communication unit 38 receives, from the CCU 14, a driving signal meant for controlling the zooming function and the focusing function of the optical lens 22.

[Configuration of CCU]

Figure 3:
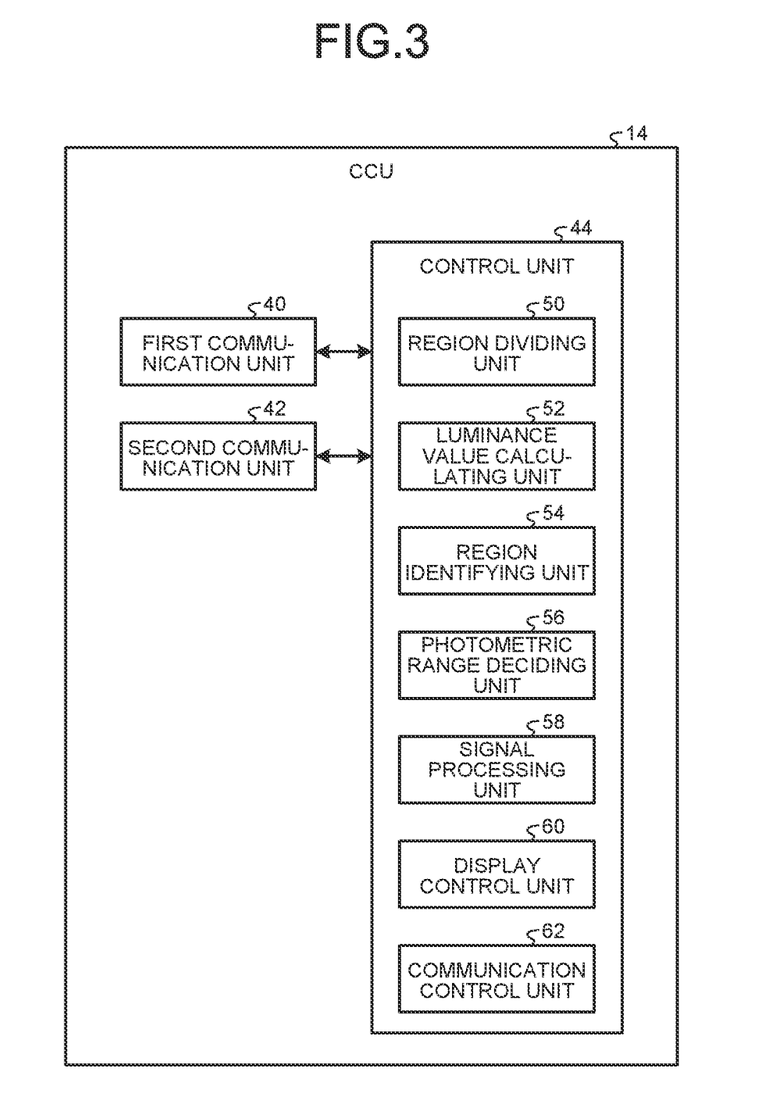
FIG. 3 is a block diagram illustrating an exemplary configuration of a CCU according to the embodiment.

Explained below with reference to FIG. 3 is an exemplary configuration of the CCU according to the embodiment. FIG. 3 is a block diagram illustrating an exemplary configuration of the CCU according to the embodiment.

The CCU 14 includes a first communication unit 40, a second communication unit 42, and a control unit 44. The CCU 14 is a control device that comprehensively controls the camera head 12 and the display device 16.

The first communication unit 40 sends a variety of information to and receives a variety of information from the camera head 12. For example, the first communication unit 40 receives an imaging signal that is input from the camera head 12 via the cable 26. Then, the first communication unit 40 outputs the imaging signal, which is received from the camera head 12, to the control unit 44. Moreover, the first communication unit 40 sends a driving signal, which is meant for controlling the driving of the camera head 12, to the camera head 12 via the cable 26.

The second communication unit 42 sends a variety of information to and receives a variety of information from the display device 16. For example, the second communication unit 42 sends an imaging signal to the display device 16 via the cable 28.

The control unit 44 controls, for example, the imaging operation of the camera head 12 and a variety of processing related to the display operation of the display device 16. For example, the control unit 44 generates a driving signal meant for controlling the driving of the camera head 12. In the present embodiment, the control unit 44 generates a driving signal meant for bringing the operator-desired body part into focus.

The control unit 44 is implemented when a CPU or an MPU executes a program, which is stored in a memory unit (not illustrated), using a RAM as the work area. Alternatively, the control unit 44 can be implemented using an integrated circuit such as an ASIC or an FPGA. Still alternatively, the control unit 44 can be implemented using a combination of software and hardware.

The control unit 44 includes a region dividing unit 50, a luminance value calculating unit 52, a region identifying unit 54, a photometric range deciding unit 56, a signal processing unit 58, a display control unit 60, and a communication control unit 62.

The region dividing unit 50 performs a division operation with respect to a taken image that is received by the first communication unit 40. For example, the region dividing unit 50 divides the taken image, which is received by the first communication unit 40, into a plurality of regions.

Figure 4:
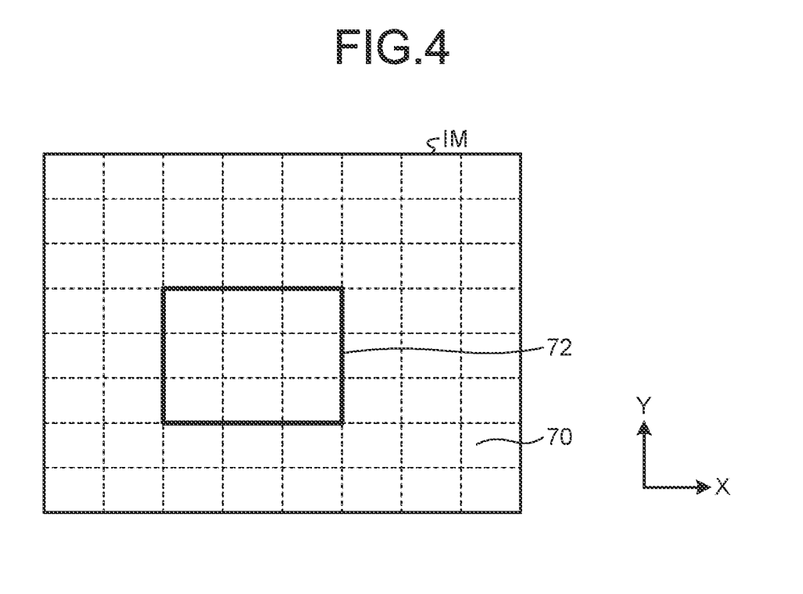
FIG. 4 is a diagram for explaining an operation of dividing a taken image into regions.

FIG. 4 is a diagram for explaining the operation of dividing a taken image into regions. With reference to FIG. 4, the direction parallel to the X axis represents the horizontal direction, and the direction parallel to the Y axis represents the vertical direction. In FIG. 4, a taken image IM is illustrated. The region dividing unit 50 divides the taken image IM into a plurality of regions 70. For example, the region dividing unit 50 divides the taken image IM into eight regions in the horizontal direction and eight regions in the vertical direction, and thus divides the taken image IM1 into 64 regions 70. Herein, the division count of the taken image IM and the dimensions of the regions 70 set in the region dividing unit 50 are arbitrary, and can be arbitrarily changed according to the design.

Returning to the explanation with reference to FIG. 3, the luminance value calculating unit 52 calculates the luminance value of the taken image. For example, the luminance value calculating unit 52 calculates the luminance value of each region in the taken image IM as obtained by division by the region dividing unit 50. For example, the luminance value calculating unit 52 calculates the average luminance value of each region in the taken image IM as obtained by division by the region dividing unit 50.

Based on the calculation result obtained by the luminance value calculating unit 52, the region identifying unit 54 identifies a predetermined region. Thus, based on the calculation obtained by the luminance value calculating unit 52, the region identifying unit 54 identifies the region 70 in which the luminance value exceeds a predetermined threshold value. The predetermined threshold value implies, for example, the luminance value at which what is called overexposure occurs. However, that is not the only possible case. Meanwhile, for example, if a plurality of regions 70 exceeds the predetermined threshold value, then the region identifying unit 54 can identify the regions 70 having the maximum luminance value. In the present embodiment, at the operator-desired location of attention inside the body of the patient, when the operator intentionally reflects the light using a procedure tool, the region identifying unit 54 identifies the regions in which the luminance value is equal to or greater than the predetermined threshold value.

The photometric range deciding unit 56 decides on the photometric range. The photometric range can be the operator-desired range of attention. The photometric range deciding unit 56 decides on the photometric range based on the regions 70 that are identified by the region identifying unit 54 to have the luminance value exceeding the predetermined threshold value. If the period of time for which the average luminance value of the region identified by the region identifying unit 54 is equal to or greater than a threshold value is equal to or greater than a first predetermined period and is smaller than a second predetermined period, then the photometric range deciding unit 56 decides that the region identified by the region identifying unit 54 represents a new photometric range. The first predetermined period is, for example, approximately equal to a few seconds. However, that is not the only possible case. The second predetermined period is, for example, approximately equal to few tens of seconds. However, that is not the only possible case. More particularly, the period of time equal to or greater than the first predetermined period and smaller than the second predetermined period is large enough to enable determination of the fact that the operator is intentionally reflecting the light using a procedure tool. In the example illustrated in FIG. 4, the photometric range deciding unit 56 decides on, for example, a photometric range 72. Herein, the photometric range 72 is a region equivalent to nine regions 70. As illustrated in FIG. 4, the photometric range is not limited to be the smallest unit such as a single region 70, and can be a region such as the photometric range 72 formed by a plurality of regions 70 representing the smallest units. Moreover, according to the features of the detection target, the photometric range 72 can appropriately change to be horizontally long or vertically long.

The signal processing unit 58 performs a variety of processing with respect to the imaging signal received from the first communication unit 40. For example, the signal processing unit 58 performs imaging auto-control such as autofocusing, automatic gain control, and automatic white balance control. Moreover, the signal processing unit 58 can perform other known types of processing with respect to the photometric range 72 decided by the photometric range deciding unit 56.

In the autofocusing control, for example, in the taken image IM, the signal processing unit 58 extracts, for each region 70, the high-range component and the midrange component of the imaging signal. For example, the signal processing unit 58 calculates the optimum driving state of the optical lens 30 in which the ratio of the high-range component and the midrange component, from among the imaging components of the photometric range 72 decided by the photometric range deciding unit 56, is the highest. In the autofocusing control, the signal processing unit 58 outputs a driving signal meant for controlling the optical lens 30 in the optimum driving state. As a result, the optical lens 30 becomes able to bring the photometric range 72, which is decided by the photometric range deciding unit 56, into focus.

In the automatic gain control, for example, in the taken image IM, the signal processing unit 58 performs gain adjustment based on the average luminance value and the maximum luminance value of each region 70. For example, the signal processing unit 58 applies gain to the imaging signal of the taken image IM in such a way that the photometric range 72, which is decided by the photometric range deciding unit 56, has the same luminance value as the target luminance value. As a result, an easy-to-view video level is achieved.

In the automatic white balance control, for example, in the taken image IM, the signal processing unit 58 calculates the RGB components in each region 70. For example, with respect to an achromatic photographic subject included in the photometric range decided by the photometric range deciding unit 56, the signal processing unit 58 achieves the optimum white balance by applying gain in such a way that the RGB components have the same level to each other.

The display control unit 60 controls the display device 16. The display control unit 60 displays, for example, the taken image IM in the display device 16. For example, in the display device 16, the display control unit 60 displays the taken image IM that has been subjected to imaging auto-control.

The communication control unit 62 controls the first communication unit 40 for controlling the communication between the camera head 12 and the CCU 14. For example, the communication control unit 62 controls the first communication unit 40 and sends, to the camera head 12, a driving signal meant for controlling the driving state of the optical lens 30.

Moreover, the communication control unit 62 controls the second communication unit 42 for controlling the communication between the CCU 14 and the display device 16. For example, the communication control unit 62 controls the second communication unit 42 and sends an imaging signal regarding the taken image to be displayed in the display device 16.

[Control Operation]

Figure 5:
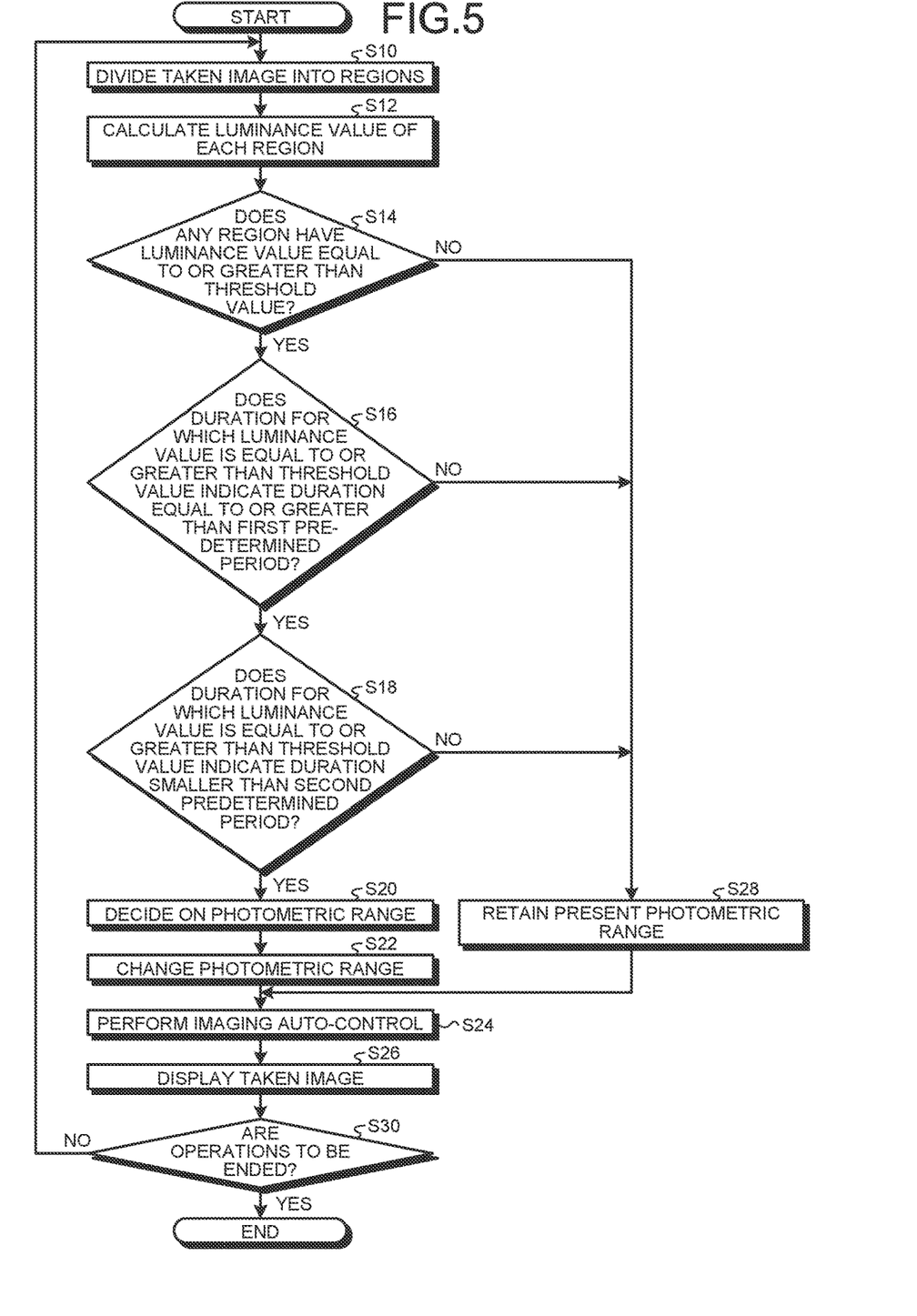
FIG. 5 is a flowchart for explaining an exemplary flow of a CCU control operation according to the embodiment.

Explained below with reference to FIG. 5 is a CCU control operation according to the embodiment. FIG. 5 is a flowchart for explaining an exemplary flow of the CCU control operation according to the embodiment.

The control unit 44 divides the taken image into a plurality of regions (Step S10). More particularly, the region dividing unit 50 divides the taken image IM into a plurality of regions 70 as illustrated in FIG. 4. Then, the system control proceeds to Step S12.

Figure 6:
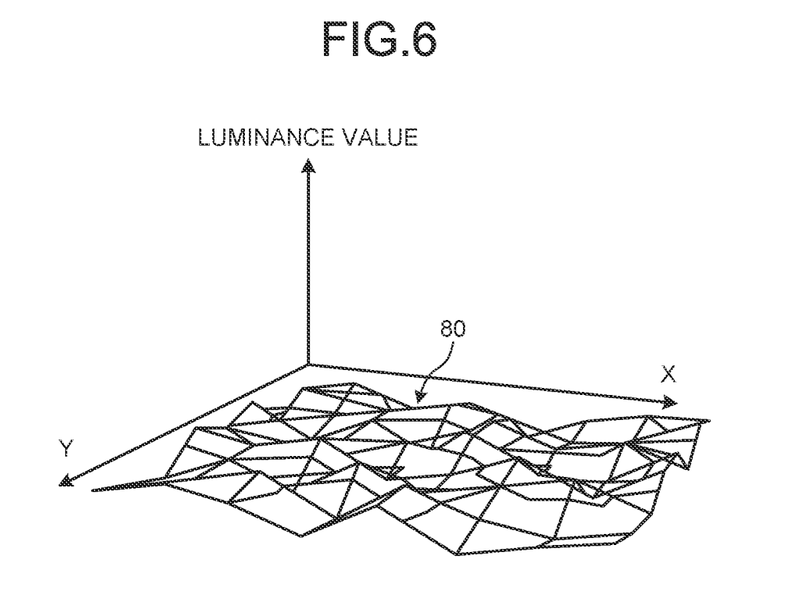
FIG. 6 is a diagram that visually illustrates the average luminance values in a taken image.

The control unit 44 calculates the luminance value of each region (Step S12). More particularly, in the taken image IM, the luminance value calculating unit 52 calculates the average luminance value of each region 70. FIG. 6 is a diagram that visually illustrates the average luminance values in the taken image IM. In FIG. 6 are illustrated the region-by-region luminance values. As illustrated in FIG. 6, as a result of calculating the average luminance value of each region 70, the luminance value calculating unit 52 can obtain luminance value information 80 in which the luminance values are visually illustrated in the form of asperity. Then, the system control proceeds to Step S14.

The control unit 44 determines whether or not any region has the luminance value to be equal to or greater than a threshold value (Step S14). More particularly, based on the luminance value of each region 70 as calculated by the luminance value calculating unit 52, the region identifying unit 54 determines whether or not any region 70 has the luminance value equal to or greater than a predetermined luminance value.

Figure 7:
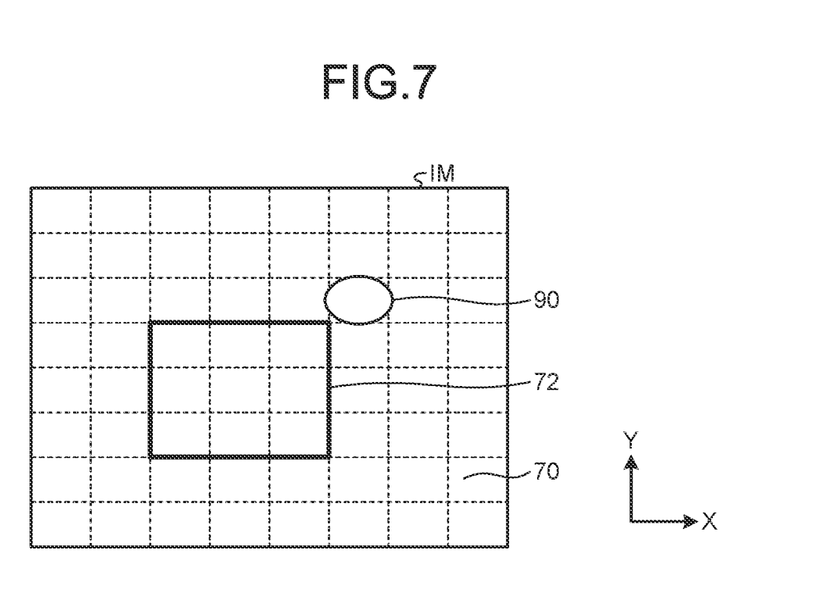
FIG. 7 is a diagram for explaining the condition in which a luminance value becomes equal to or greater than a predetermined threshold value.
Figure 8:
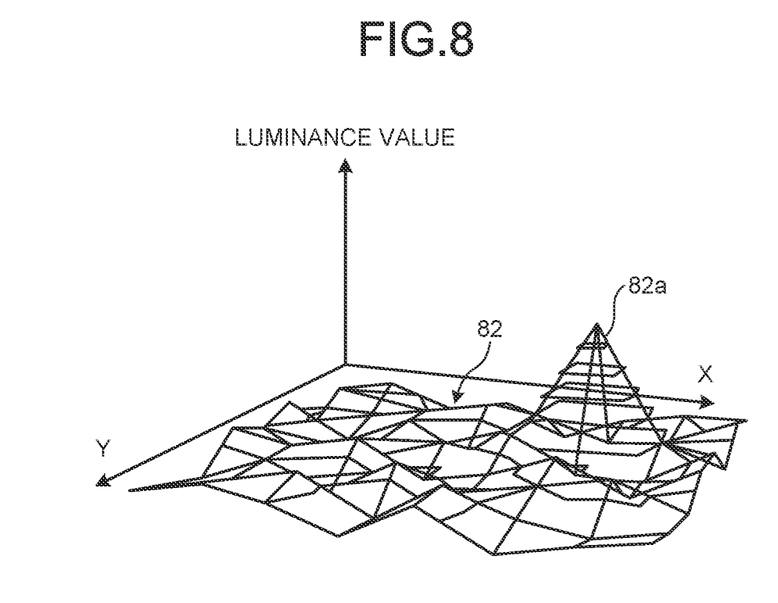
FIG. 8 is a diagram that visually illustrates the average luminance values in a taken image in which a reflecting object is captured.

Explained below with reference to FIG. 7 is the condition in which a luminance value becomes equal to or greater than a predetermined threshold value. FIG. 7 is a diagram for explaining the condition in which a luminance value becomes equal to or greater than a predetermined threshold value. As illustrated in FIG. 7, a reflecting object 90 is captured in the taken image IM. In the present embodiment, the reflecting object 90 represents a procedure tool such as a surgical knife used by the operator. FIG. 8 is a diagram that visually illustrates the luminance values in the taken image IM in which a reflecting object is captured. In FIG. 8 is illustrated luminance value information 82 indicating the region-by-region luminance values. The luminance value information 82 contains a high-luminance region 82a in which the luminance value is prominently high due to the reflection from the reflecting object 90. For example, the region identifying unit 54 detects the high-luminance region 82a based on the luminance value information 82, and identifies it as the region having the luminance value equal to or greater than a predetermined threshold value. Thus, if a region having the luminance value to be equal to or greater than a threshold value is determined to be present (Yes at Step S14), then the system control proceeds to Step S16. On the other hand, if a region having the luminance value to be equal to or greater than a threshold value is determined to be absent (No at Step S14), then the system control proceeds to Step S28.

If the determination at Step S14 indicates Yes, then the control unit 44 determines whether or not, in the identified region, the duration for which the luminance value is equal to or greater than the threshold value is equal to or greater than the first predetermined period (Step S16). More particularly, the photometric range deciding unit 56 uses a counter (not illustrated) to determine whether or not the duration for which the luminance value is equal to or greater than the threshold value is equal to or greater than the first predetermined period. If the duration for which the luminance value is equal to or greater than the threshold value is determined to be equal to or greater than the first predetermined period (Yes at Step S16), then the system control proceeds to Step S18. On the other hand, if the duration for which the luminance value is equal to or greater than the threshold value is determined not to be equal to or greater than the first predetermined period (No at Step S16), then the system control proceeds to Step S28.

If the determination at Step S16 indicates Yes, then the control unit 44 determines whether or not, in the identified region, the duration for which the luminance value is equal to or greater than the threshold value is smaller than the second predetermined period (Step S18). More particularly, the photometric range deciding unit 56 uses a counter (not illustrated) to determine whether or not the duration for which the luminance value is equal to or greater than the threshold value is smaller than the second predetermined period. If the duration for which the luminance value is equal to or greater than the threshold value is determined to be smaller than the second predetermined period (Yes at Step S18), then the system control proceeds to Step S20. On the other hand, if the duration for which the luminance value is equal to or greater than the threshold value is determined not to be smaller than the second predetermined period (No at Step S18), then the system control proceeds to Step S28.

If the determination at Step S18 indicates Yes, then the control unit 44 decides on the photometric range (Step S20). More particularly, the photometric range deciding unit 56 decides that the region identified by the region identifying unit 54 at Step S14 represents the new photometric range. Then, the system control proceeds to Step S22.

The control unit 44 changes the photometric range (Step S22). More particularly, the photometric range deciding unit 56 changes the present photometric range to the new photometric range decided at Step S20.

Figure 9:
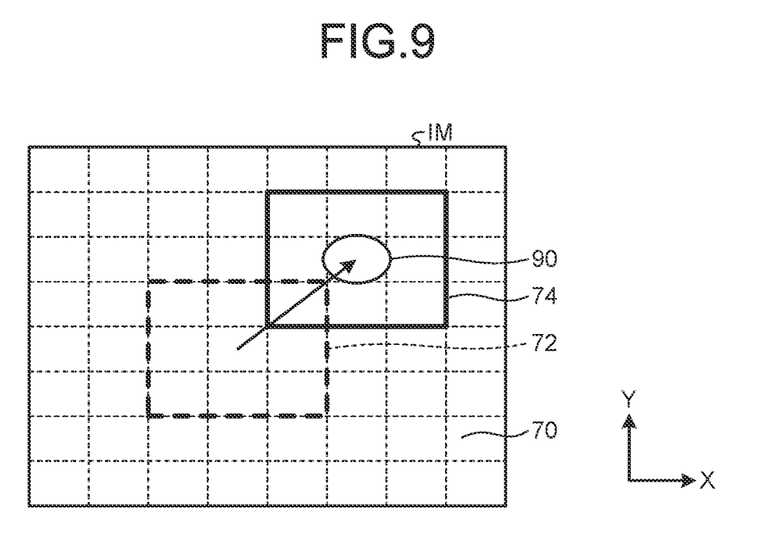
FIG. 9 is a diagram for explaining a method for changing the photometric range.

Explained below with reference to FIG. 9 is a method for changing the photometric range. FIG. 9 is a diagram for explaining a method for changing the photometric range. In the normal auto-gain control, if momentary changes in the signal are followed, then the brightness of the image undergoes severe changes and the video becomes more obscure. Hence, the photometric range is changed while keeping a time constant of a few seconds to few tens of seconds. In the present embodiment, the region having the luminance value equal to or greater than the threshold value is used as the index of the target coordinates of the photometric range. More particularly, as illustrated in FIG. 9, the photometric range deciding unit 56 changes the present photometric range 72 to a photometric range 74 centered around the reflecting object 90. As a result of performing such control, the movement of the photometric range intended for the practitioner or the assistant of the practitioner can be easily performed only by a small action using the procedure tool of the practitioner. Subsequently, the system control proceeds to Step S24.

The control unit 44 performs imaging auto-control (Step S24). More particularly, with respect to the photometric range changed at Step S22, the signal processing unit 58 performs imaging auto-control such as autofocusing, automatic gain control, and automatic white balance control. Then, the system control proceeds to Step S26.

The control unit 44 displays an image in the display device 16 (Step S26). More particularly, the display control unit 60 displays, in the display device 16, the taken image that has been subjected to imaging auto-control by the signal processing unit 58 at Step S24. Then, the system control proceeds to Step S30.

If the determination Step S14 indicates No, or if the determination Step S16 indicates No, or if the determination Step S18 indicates No, then the control unit 44 retains the present photometric range (Step S28). More particularly, the photometric range deciding unit 56 retains the present photometric range without changing it. More particularly, when the determination Step S16 indicates No, that is, when the duration for which the luminance value is equal to or greater than the threshold value is smaller than the first predetermined period, the photometric range deciding unit 56 retains the present photometric range under the assumption that the reflection is not intentionally caused by the operator. When the determination Step S18 indicates No, that is, when the duration for which the luminance value is equal to or greater than the threshold value is equal to or greater than the second predetermined period, the photometric range deciding unit 56 retains the present photometric range under the assumption that the reflection is originally present regardless of the intention of the operator. Then, the system control proceeds to Step S24.

The control unit 44 determines whether or not to end the control operation (Step S30). More particularly, when an operation for ending the control operation is received and when an operation for switching off the power source is received, the control unit 44 determines to end the control operation. If it is determined to end the control operation (Yes at Step S30), then the operations illustrated in FIG. 6 are ended. On the other hand, if it is determined not to end the control operation (No at Step S30), then the system control returns to Step S10.

As explained above, in the present embodiment, in a taken image, a certain range centered around a region having the luminance value to be equal to or greater than a threshold value is set as the photometric range to be subjected to imaging auto-control. As a result, in the present embodiment, the most suitable image processing can be performed with respect to the location on which the operator is focusing attention. In the present embodiment, the operator can move a procedure tool for reflecting the light, so that the photometric range can be changed with ease.

Moreover, in the present embodiment, the photometric range can be retained with the aim of ensuring that, once the procedure is completed, the light does not get reflected from the procedure tool. Thus, in the present embodiment, as a result of fixing the photometric range to the location of performing procedure, the post-procedure condition becomes easy to observe.

In the present embodiment, it is possible to make use of the features of the photographing conditions of a laparoscopic surgery in which a rigid endoscope is used. As a result, in the present embodiment, during a laparoscopic surgery in which a rigid endoscope is used, the photometric range can be set at the location on which the operator is focusing attention, and optimum imaging auto-control can be performed.

Herein, although the application concerned is described with reference to the abovementioned embodiment for a complete and clear disclosure, the appended claims are not to be thus limited but are to be construed as embodying all modifications and alternative constructions that may occur to one skilled in the art that fairly fall within the basic teaching herein set forth. Moreover, the constituent elements explained above can be appropriately combined.

Furthermore, the constituent elements can be deleted, substituted, or modified without departing from the scope of the embodiment described above.

INDUSTRIAL APPLICABILITY

An imaging control device, an endoscope system, and an imaging control method according to present embodiment can be used in, for example, a medical device.

According to the application concerned, it becomes possible to perform imaging auto-control by setting the operator-desired body part as the photometric range.

What is claimed is:
1. An imaging control device comprising:
a region dividing unit that divides a taken image into a plurality of regions;

a luminance value calculating unit that calculates average luminance value of each region obtained by division by the region dividing unit;

a region identifying unit that identifies a region in which the average luminance value calculated by the luminance value calculating unit is equal to or greater than a predetermined threshold value;

a photometric range deciding unit that, when period of time for which average luminance value of the region identified by the region identifying unit is equal to or greater than the threshold value is a period of time equal to or greater than a first predetermined period and smaller than a second predetermined period, decides that the region identified by the region identifying unit represents a new photometric range; and a signal processing unit that performs imaging auto-control with respect to the new photometric range decided by the photometric range deciding unit.

2. The imaging control device according to claim 1, wherein, when period of time for which average luminance value of the region identified by the region identifying unit is equal to or greater than the threshold value is a period of time either smaller than the first predetermined period or equal to or greater than the second predetermined period, the photometric range deciding unit does not change photometric range.

3. The imaging control device according to claim 1, wherein when period of time for which average luminance value of the region identified by the region identifying unit is equal to or greater than the threshold value is a period of time equal to or greater than the first predetermined period and smaller than the second predetermined period, and when a plurality of regions has average luminance value to be equal to or greater than the threshold value, the photometric range deciding unit decides that region having highest average luminance value represents new photometric range.

4. An endoscope system comprising:

the imaging control device according to claim 1;

an imaging device that, under control of the imaging control device, takes image of an affected area; and a light source that is installed in the imaging device and that bombards light onto the affected area, wherein the imaging control device decides on new photometric range based on change in luminance value attributed to reflected light that is formed by reflection of the light, which is bombarded by the light source unit, from a procedure tool.

5. An imaging control method comprising:

a step for dividing a taken image into a plurality of regions;

a step for calculating average luminance value of each region obtained by division;

a step for identifying a region in which the calculated average luminance value is equal to or greater than a predetermined threshold value;

a step for deciding that, when period of time for which average luminance value of the identified region is equal to or greater than the threshold value is a period of time equal to or greater than a first predetermined period and smaller than a second predetermined period, includes deciding on the identified region as a new photometric range; and a step for performing imaging auto-control with respect to the new photometric range.

* * * * *